US009031635B2

(12) United States Patent
Sugiura et al.

(10) Patent No.: US 9,031,635 B2
(45) Date of Patent: *May 12, 2015

(54) MRI DIFFUSION WEIGHTED IMAGING WITH ESTIMATED MOTION PROBING GRADIENT B-FACTORS BASED ON ACQUIRED APPARENT DIFFUSION COEFFICIENTS FOR EACH PIXEL

(71) Applicants: Kabushiki Kaisha Toshiba, Minato-ku, Tokyo (JP); Toshiba Medical Systems Corporation, Otawara-shi, Tochigi (JP)

(72) Inventors: Satoshi Sugiura, Otawara (JP); Tokunori Kimura, Yaita (JP); Mitsukazu Kamata, Nasushiobara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/243,268

(22) Filed: Apr. 2, 2014

(65) Prior Publication Data
US 2014/0212017 A1 Jul. 31, 2014

Related U.S. Application Data

(62) Division of application No. 12/569,273, filed on Sep. 29, 2009, now Pat. No. 8,805,473.

(30) Foreign Application Priority Data

Sep. 29, 2008 (JP) .................................. 2008-251683
Jul. 16, 2009 (JP) .................................. 2009-167866

(51) Int. Cl.
*A61B 5/05* (2006.01)
*G01R 33/56* (2006.01)
(Continued)

(52) U.S. Cl.
CPC ............ *G01R 33/5602* (2013.01); *A61B 5/055* (2013.01); *A61B 5/7285* (2013.01); *G01R 33/543* (2013.01); *G01R 33/56341* (2013.01); *G06T 11/003* (2013.01)

(58) Field of Classification Search
USPC .................... 600/407, 410–423; 324/300–315
See application file for complete search history.

(56) References Cited

U.S. PATENT DOCUMENTS 5,572,124 A * 11/1996 Bito et al. ...................... 324/307
5,786,692 A * 7/1998 Maier et al. ................... 324/307
(Continued)

FOREIGN PATENT DOCUMENTS

JP 9-173315 7/1997
JP 2008-012172 1/2008
(Continued)

OTHER PUBLICATIONS

Chinese office action dated Sep. 8, 2011, issued in CN 2009-10204450.1.
(Continued)

*Primary Examiner* — James Kish
(74) *Attorney, Agent, or Firm* — Nixon & Vanderhye P.C.

(57) ABSTRACT

A magnetic resonance diagnostic apparatus includes a derivation unit to derive an apparent diffusion coefficient regarding a pixel position for each pixel position included in a region of interest in at least two original images obtained by imaging a same imaging region of a same subject using at least two b-factors that are different from each other, respectively, based on pixel values of each of at least two original images regarding the pixel positions, and a first estimation unit to estimate a pixel value obtained by using a b-factor that is different from the at least two b-factors, regarding each pixel position included in the region of interest, based on the apparent diffusion coefficient derived for each pixel position.

7 Claims, 7 Drawing Sheets

(51) Int. Cl.
*A61B 5/055* (2006.01)
*G01R 33/563* (2006.01)
*G06T 11/00* (2006.01)
*A61B 5/00* (2006.01)
*G01R 33/54* (2006.01)

(56) References Cited

U.S. PATENT DOCUMENTS

| | | | |
|---|---|---|---|
| 6,288,540 B1* | 9/2001 | Chen et al. | 324/300 |
| 6,751,495 B2* | 6/2004 | Maier et al. | 600/410 |
| 7,015,696 B2* | 3/2006 | Kabasawa | 324/318 |
| 7,560,926 B2* | 7/2009 | Meredith et al. | 324/309 |
| 2001/0039377 A1* | 11/2001 | Maier et al. | 600/410 |
| 2003/0160612 A1* | 8/2003 | Yablonskiy et al. | 324/309 |
| 2005/0134266 A1* | 6/2005 | Kabasawa | 324/309 |
| 2009/0096448 A1* | 4/2009 | Meredith et al. | 324/309 |
| 2010/0253342 A1* | 10/2010 | Kimura | 324/309 |
| 2011/0043206 A1* | 2/2011 | Kimura et al. | 324/309 |
| 2011/0280456 A1* | 11/2011 | Sussman et al. | 382/131 |
| 2013/0033262 A1* | 2/2013 | Porter | 324/309 |

FOREIGN PATENT DOCUMENTS

| | | |
|---|---|---|
| JP | 2008-093418 | 4/2008 |
| JP | 2008-136871 | 6/2008 |

OTHER PUBLICATIONS

Da Xing, et al., "Optimised Diffusion-Weighting for Measurement of Apparent Diffusion Coefficient (ADC) in Human Brain," *Magnetic Resonance Imaging*, vol. 15, No. 7, pp. 771-784 (1997).

Office Action mailed on Jul. 30, 2013, in JP 2009-167866 (including English translation).

* cited by examiner

|  | $b_a$ | $b_b$ | $b_c$ | $b_1$ | $b_2$ | $b_3$ |
|---|---|---|---|---|---|---|
| Head | 0 | 1000 | — | 1500 | 2000 | — |
| Breast | 0 | 600 | 1000 | 1500 | 2000 | 3000 |
| Liver | 0 | 700 | — | 1000 | 1500 | 2000 |
| Female pelvis | 0 | 700 | — | 1000 | 1500 | — |
| Prostate gland | 0 | 500 | 1000 | 1500 | 2000 | 2500 |
| ⋮ | ⋮ | ⋮ | ⋮ | ⋮ | ⋮ | ⋮ |

F I G. 7

| Imaging portion | Diffusion coefficient $(mm^2/sec)$ |
|---|---|
| Head | 0.6 |
| Breast | 1.0 |
| Liver | 1.5 |
| Female pelvis | 1.7 |
| Prostate gland | 1.0 |
| ⋮ | ⋮ |

FIG. 9

MRI DIFFUSION WEIGHTED IMAGING WITH ESTIMATED MOTION PROBING GRADIENT B-FACTORS BASED ON ACQUIRED APPARENT DIFFUSION COEFFICIENTS FOR EACH PIXEL

CROSS-REFERENCE TO RELATED APPLICATIONS

This is a division of U.S. Ser. No. 12/569,273 filed Sep. 29, 2009, which claims priority under 35 U.S.C. §119 based upon Japanese Patent Application No. 2008-251683 filed Sep. 29, 2008, and Japanese Patent Application No. 2009-167866 filed Jul. 16, 2009, the entire contents of all of which are incorporated herein by reference.

BACKGROUND

1. Technical Field

The present exemplary embodiments are related to a magnetic resonance diagnostic apparatus and a magnetic resonance diagnostic method that use magnetic resonance phenomenon to obtain an image of a subject.

2. Description of Related Art

In diffusion weighted imaging (DWI), a pair of motion probing gradients (MPG) is added upon imaging. Further, a diffusion weighted image is obtained by imaging a signal difference that appears depending on the extent of phase diffusion of a spin of a proton transferred by diffusion while applying the MPG.

As a value to indicate the impact of an MPG pulse, a b-factor is used. When the b-factor is increased, a contrast due to diffusion becomes stronger, and an image that further reflects a diffusion phenomenon is obtained. This b-factor is expressed by the following equation.

$$b = (2\pi)^2 \int_0^{TE} \vec{k}(t) \cdot \vec{k}(t) dt$$

$$\vec{k}(t) = \frac{\gamma}{2\pi} \int_0^t \vec{G}(t') dt'$$

When an imaging sequence is a widely used single shot SE-EPI (spin echo-echo planar imaging), and in a case where the MPG pulse is applied uniaxially as an ideal Block pulse, the b-factor is expressed by the following equation.

$$b = \gamma^2 G^2 \delta^2 (\Delta - \delta/3)$$

Further, G indicates a maximum gradient magnetic field intensity, δ indicates time for applying the MPG pulse, and Δ indicates time difference of the center of two MPG pulse wave forms.

In other words, the b-factor is proportionate to the square of the maximum gradient magnetic field intensity C, or the square of time for applying the MPG pulse.

A thousand or so b-factors widely used in DWI give low diffusion weighted contrast, and a poor portrait of malignant tumor. Therefore, it is desired that the b-factor be increased to improve diffusion weighted contrast. However, if the time δ for applying MPG pulse is increased to increase the b-factor, the TE (echo time) becomes extended, thereby causing SNR (signal-to-noise ratio) to deteriorate and motion artifact to increase. However, in order to increase maximum gradient magnetic field intensity G to obtain a large b-factor while maintaining a constant TE, it is necessary to improve the hardware performance of the gradient magnetic field system, which requires the cost to increase.

Further, JP-A 2008-12172 (KOKAI) (US 2008/0007264 A1) discloses a technique to generate an image for reading X-rays by processing a DWI image.

BRIEF SUMMARY

Under the above mentioned circumstances, it has been desired to enable obtaining a diffusion weighted image using a b-factor that is larger than what corresponds to the maximum gradient magnetic field intensity and time for applying the MPG pulse.

According to a first embodiment of the present invention, there is provided a magnetic resonance diagnostic apparatus comprising: a derivation unit to derive an apparent diffusion coefficient regarding a pixel position for each pixel position included in a region of interest in at least two original images obtained by imaging a same imaging region of a same subject using at least two b-factors that are different from each other, respectively, based on pixel values of each of at least two original images regarding the pixel positions; and a first estimation unit to estimate a pixel value obtained by using a b-factor that is different from the at least two b-factors, regarding each pixel position included in the region of interest, based on the apparent diffusion coefficient derived for each pixel position.

According to a second embodiment of the present invention, there is provided a magnetic resonance diagnostic method comprising: deriving an apparent diffusion coefficient regarding a pixel position for each pixel position included in a region of interest in at least two original images obtained by imaging a same imaging region of a same subject using at least two b-factors that are different from each other, respectively, based on pixel values of each of at least two original images regarding the pixel positions; and estimating a pixel value obtained by using a b-factor that is different from the at least two b-factors, regarding each pixel position included in the region of interest, based on the apparent diffusion coefficient derived for each pixel position.

According to a third embodiment of the present invention, there is provided a magnetic resonance diagnostic apparatus comprising: an imaging unit to image at least two original images by imaging a same imaging region of a same subject using each of at least two b-factors that are different from each other; and an estimation unit to estimate a pixel value obtained by using a b-factor that is different from the at least two b-factors, regarding each pixel position included in a region of interest in the original image, based on pixel values in each of the at least two original images regarding pixel positions.

Additional objects and advantages of the invention will be set forth in the description that follows and, in part, will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate exemplary embodiments of the invention, and together with the general description given above and the detailed description of the embodiments given below, serve to explain the principles of the invention.

FIG. 7 shows an example of an information table stored in a storage unit in FIG. 1 in the second embodiment.

FIG. 9 shows an example of an information table stored in a storage unit in FIG. 1 in the third embodiment.

DETAILED DESCRIPTION OF EXEMPLARY EMBODIMENTS

Exemplary embodiments of the present invention will be hereinafter described with reference to the drawings.

Figure 1:
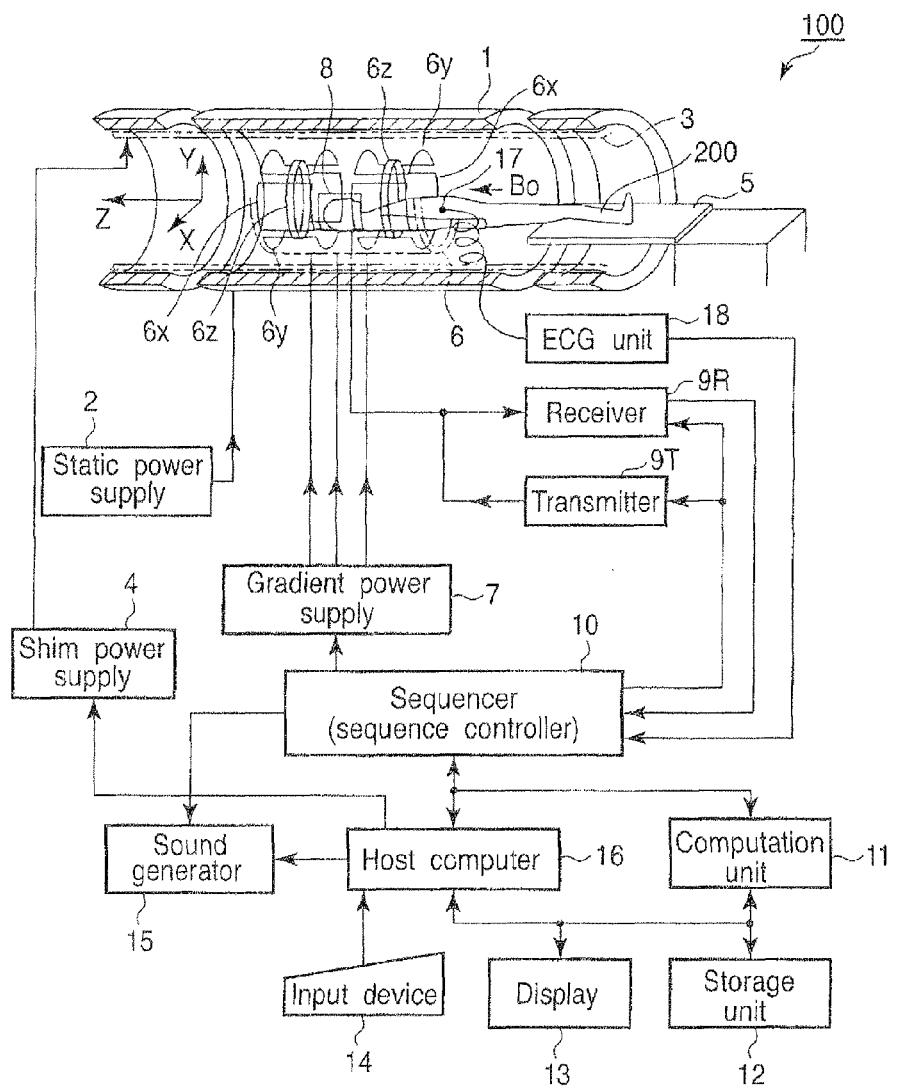
FIG. 1 is a diagram showing a schematic configuration of a magnetic resonance diagnostic apparatus according to an embodiment of the present invention.

FIG. 1 is a diagram showing the schematic configuration of a magnetic resonance diagnostic apparatus 100 according to the present embodiments.

The magnetic resonance diagnostic apparatus 100 comprises a bed unit, a static-magnetic-field generating unit, a gradient-magnetic-field generating unit, a receiving/transmitting unit, and a control/operating unit. The bed unit moves a subject 200 mounted thereon. The static-magnetic-field generating unit generates a static magnetic field. The gradient-magnetic-field generating unit generates a gradient magnetic field designed to add position information to the static magnetic field. The receiving/transmitting unit receives and transmits a radio-frequency signal. The control/operating unit controls the whole system and reconstructs images. The magnetic resonance diagnostic apparatus 100 has, as components of these units, a magnet 1, a static magnetic power supply 2, a shim coil 3, a shim power supply 4, a top plate 5, a gradient coil unit 6, a gradient power supply 7, an RF coil unit 8, a transmitter 9T, a receiver 9R, a sequencer (sequence controller) 10, a computation unit 11, a storage unit 12, a display 13, an input device 14, a sound generator 15, and a host computer 16. Connected to the magnetic resonance diagnostic apparatus 100 is an electrocardiograph unit that measures an ECG signal as a signal representing the cardiac pulsation of the subject 200.

The static-magnetic-field generating unit includes the magnet 1, the static magnetic power supply 2, the shim coil 3 and the shim power supply 4. For example, a superconducting magnet or a normal conducting magnet can be used as the magnet 1. The static magnetic power supply 2 supplies a current to the magnet 1. In addition, the static magnetic power supply 2 can be omitted when the superconducting magnet is employed as the magnet 1. The static-magnetic-field generating unit therefore generates a static magnetic field $B_0$ in a cylindrical space (diagnostic space) into which the subject 200 is moved. The direction of the static magnetic field $B_0$ virtually coincides with the axial direction (Z-axis direction) of the diagnostic space. The shim coil 3 generates a correction magnetic field for rendering the static magnetic field uniform when a current is supplied to it from the shim power supply 4 under the control of the host computer 16.

The bed unit moves the top plate 5, on which the subject 200 is lying, into or out of the diagnostic space.

The gradient-magnetic-field generating unit includes the gradient coil unit 6 and the gradient power supply 7. The gradient coil unit 6 is arranged in the magnet 1. The gradient coil unit 6 has three coils 6x, 6y and 6z that generate gradient magnetic fields extending in mutually orthogonal X-, Y- and Z-axes, respectively. The gradient power supply 7 supplies pulse currents for generating gradient magnetic fields to the coils 6x, 6y and 6z, under the control of the sequencer 10. The gradient-magnetic-field generating unit controls the pulse currents supplied from the gradient power supply 7 to the coils 6x, 6y and 6z. Thus, the gradient-magnetic-field generating unit synthesizes gradient magnetic fields extending in the three physical axes (the X-, Y- and Z-axes), respectively. The unit sets these magnetic fields in logical axes defined by a slice direction gradient magnetic field Gs, a phase-encode direction gradient magnetic field Ge and a read-out direction (frequency-encode) gradient magnetic field Gro, respectively, which intersect at right angles with one another. The slice, phase-encode and read-out direction gradient magnetic fields, Gs, Ge and Gr are superposed on the static magnetic field $B_0$.

The receiving/transmitting unit includes the RF coil unit 8, the transmitter 9T, and the receiver 9R. The RF coil unit 8 is arranged in the vicinity of the subject 200 in the diagnostic space. The transmitter 9T and the receiver 9R are connected to the RF coil unit 8. The transmitter 9T and the receiver 9R operate under the control of the sequencer 10. The transmitter 9T supplies an RF current pulse of Lamar frequency to the RF coil unit 8 in order to induce nuclear magnetic resonance (NMR). The receiver 9R acquires an MR signal (radio-frequency signal), such as an echo signal, which the RF coil unit 8 has received. The receiver 9R then performs, on the MR signal, various processes, such as pre-amplification, intermediate-frequency conversion, phase detecting, low-frequency amplification and filtering. Finally, the receiver 9R performs analog-to-digital (A/D) conversion on the MR signal, producing digital data (raw data).

However, the RF coil unit 8 can be configured by an arbitrary coil that corresponds to various purposes, or by a single coil.

The control/operating unit includes the sequencer 10, the computation unit 11, the storage unit 12, the display 13, the input device 14, the sound generator 15 and the host computer 16.

The sequencer 10 has a CPU and a memory. The sequencer 10 stores, into the memory, pulse sequence information transmitted from the host computer 16. The CPU of the sequencer 10 controls the operations of the gradient power supply 7, transmitter 9T and receiver 9R in accordance with the sequence information stored in the memory. The CPU of the sequencer 10 also receives the raw data output from the receiver 9R and transfers the raw data to the computation unit 11. Note that the sequence information is all data necessary for operating the gradient power supply 7, transmitter 9T and receiver 9R in accordance with the pulse sequence. It includes, for example, information about the intensity of the pulse current supplied to the coils 6x, 6y and 6z, the period of applying the pulse current and the timing of applying the pulse current. The sequence information includes that of what realizes DWI.

The computation unit 11 receives the raw data output from the transmitter 9T, through the sequencer 10. The computation unit 11 has an internal memory. The internal memory has a k-space (also called Fourier space or frequency space), in which the raw data input to the computation unit 11 is placed. The computation unit 11 subjects the data placed in the k-space to two- or three-dimensional Fourier transform, thereby reconstructing video data for the real space. The computation unit 11 can perform, if necessary, synthesis and differential operations (including weighted differentiation) on any data representing an image. The synthesis includes cumulative addition of pixel values, maximum intensity projection (MIP), minimum intensity projection (minIP), and the like. As another example of the synthesis, the axes of several frames may be aligned in a Fourier space, and the raw data items representing these frames may be synthesized, thereby generating one-frame raw data. The addition of pixel values includes, for example, simple addition, addition averaging or weighting addition.

The storage unit 12 stores video data reconstructed or video data subjected to the above-mentioned synthesis or differential processing.

The display 13 displays various images to be presented to a user, under the control of the host computer 16. For example, a display device such as a liquid crystal display can be used as the display 13.

The input device 14 is operated to input various types of information, such as parameter information for selecting synchronization timing desired by the operator, scanning conditions, the pulse sequence, information about the image synthesis and differential operation, and the like. The input device 14 sends the input information to the host computer 16. The input device 14 comprises, as the case may be, a pointing device such as a mouse or a track ball, a selection device such as a mode change switch, or an input device such as a keyboard.

The sound generator 15 generates messages for the start and end of breath holding as sounds when instructed by the host computer 16.

The host computer 16 has various functions that can be realized by executing a predetermined software procedure. These various functions may include each of the following functions. One of the functions is to instruct pulse sequence information to the sequencer 10 and to control operation of the entire apparatus. One of the functions mentioned above is to control the sequencer 10 so that the same portion of the same subject is imaged by using each of the two respectively different b-factors. One of the functions mentioned above is to obtain apparent diffusion coefficient (ADC) regarding pixel positions for each of the pixel positions included within the region of interest in the two images respectively obtained by using the two b-factors mentioned above, based on each of the pixel values in the above two images with regard to the pixel positions. One of the functions mentioned above is to estimate pixel values obtained by using b-factors that are different from the two b-factors mentioned above, based on ADC obtained regarding each pixel position, with respect to each pixel position included within the region of interest. One of the functions mentioned above is to generate a calculated image by arranging the pixel values estimated respectively with respect to each of the pixel positions. One of the functions mentioned above is to control the display 13 so as to display the calculated image. One of the functions mentioned above is to estimate an SNR for another original image imaged using another b-factor, based on a signal value and noise level in the original image imaged using one b-factor, and a diffusion coefficient set in association with a portion of the subject included in the image region.

The electrocardiograph unit includes an ECG sensor 17 and an ECG unit 18. The ECG sensor 17 is attached to the surface of the body of the subject 200, and detects an ECG signal of the subject 200 as an electric signal (hereinafter referred to as a sensor signal). The ECG unit 18 subjects the sensor signal to various kinds of processing, including digitization, and then outputs it to the host computer 16 and the sequencer 10. For example, a vector electrocardiograph can be used as the electrocardiograph unit. The sequencer 10 uses the sensor signal generated by the electrocardiograph unit, when it is necessary to carry out a scan in synchronization with the cardiac phase of the subject 200.

First Embodiment

An operation carried out in a first embodiment of the magnetic resonance diagnostic apparatus 100 will be explained.

Figure 2:
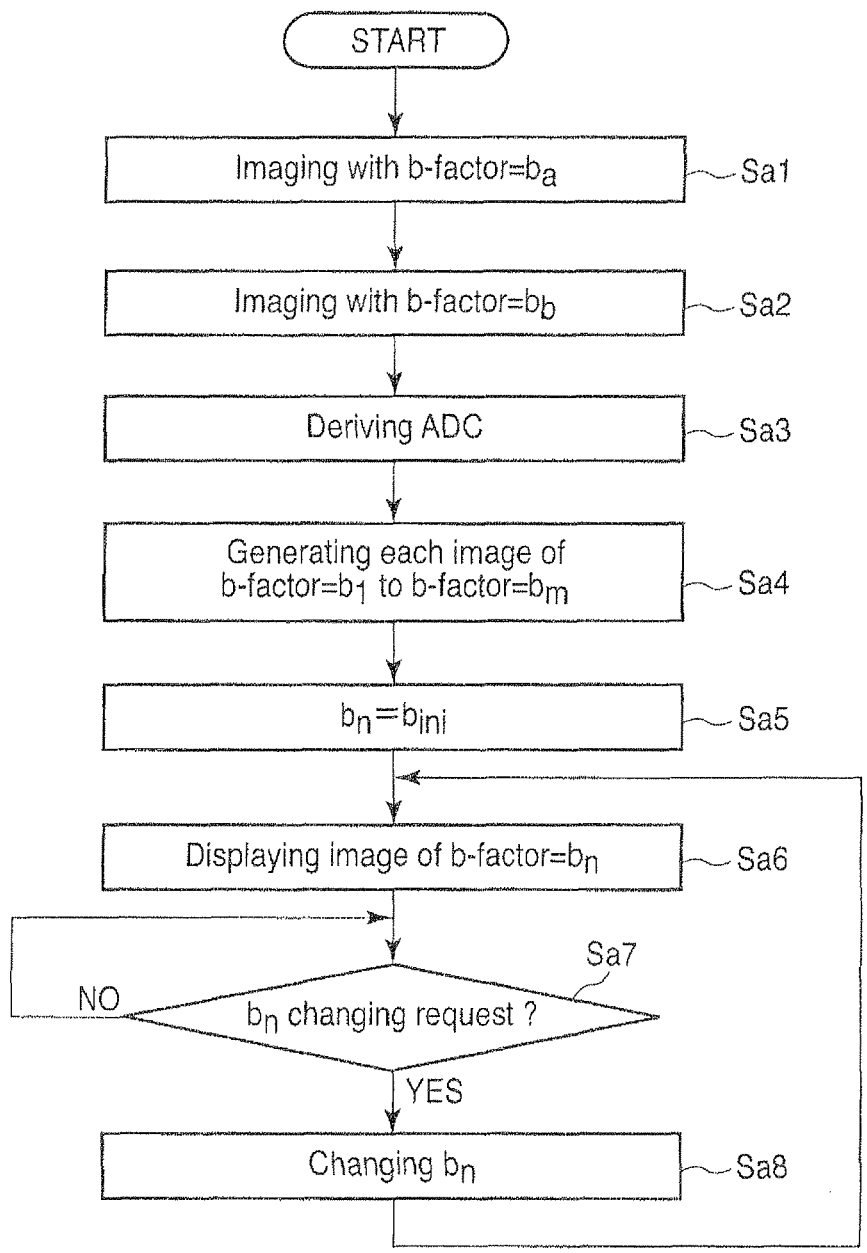
FIG. 2 is a flow chart showing a processing procedure in a first embodiment of a host computer illustrated in FIG. 1.

FIG. 2 is a flow chart showing a processing procedure in the first embodiment of the host computer 16.

In step Sa1, the host computer 16 instructs the sequencer 10 to carry out imaging in a predetermined region of interest, by setting a b-factor as a predetermined value $b_a$. In accordance with this instruction, the sequencer 10 operates the gradient power supply 7, the transmitter 9T, the receiver 9R and the computation unit 11 etc., so as to carry out imaging by using a b-factor that has value $b_a$. The image imaged here will be referred to as a first original image hereinafter.

Value $b_a$ can be an arbitrary value. However, 0 is preferable. In the case where $b_a$=0, for imaging in step Sa1, it is fine to use T2 weighted imaging by a spin echo (SE) method or a fast spin echo (FSE) method. It is also fine to use imaging by a single-shot isotropic EPI method or a stimulated echo (STE) method. By using these imaging methods, imaging time can be shortened and resolution can be improved.

In step Sa2, the host computer 16 instructs the sequencer 10 to carry out imaging regarding the region of interest, by setting the b-factor as a value $b_b$, which is predetermined to be different from value $b_a$. In accordance with this instruction, the sequencer 10 operates the gradient power supply 7, the transmitter 9T, the receiver 9R and the computation unit 11 etc., so as to carry out imaging by using a b-factor that has value $b_b$. The imaged image here will be referred to as a second original image hereinafter. In the case where neither of value $b_a$ nor $b_b$ are 0, the direction of MPG application is preferred to be mutually the same between the case of imaging the first original image and the case of imaging the second original image.

In step Sa3, the host computer 16 derives ADC respectively with regard to each pixel within the above mentioned region of interest. In the case where signal values of the first and second original images regarding a pixel of the same position are expressed respectively by S ($b_a$) and S ($b_b$), this is done by substituting these signal values in the following equation (1).

$$\text{ADC} = \log_n[S(b_b)/S(b_a)]/(b_b - b_a) \quad (1)$$

The above equation (1) is obtained by deforming the following equation (2).

$$S(b_b) = S(b_a) \cdot \exp[-(b_b - b_a) \cdot \text{ADC}] \quad (2)$$

In step Sa4, the host computer 16 generates each image (hereinafter referred to as calculated image) in the case where the b-factor is set to be from value $b_1$ to value $b_m$. Values $b_1$ to value $b_m$ are m types of values predetermined to differ respectively from value $b_a$ and value $b_b$. These value $b_1$ to value $b_m$ are, for example, values that increase in order by a constant value (such as 100).

For example, an image of b-factor=$b_1$ can be obtained by calculating the signal value of each pixel within the region of interest by the following equation (3). Equation (3) is based on the above mentioned equation (2). In equation (3), a value that is derived in step Sa3 for each pixel substitutes for ADC.

$$S(b_1)=S(b_a)\cdot\exp[-(b_1-b_a)\cdot ADC] \quad (3)$$

Further, in the case where value $b_a=0$, the following equation (4) serves to substitute for equation (3).

$$S(b_1)=S(0)\cdot\exp[-b_1\cdot ADC] \quad (4)$$

The host computer 16 stores each of the m pieces of images generated hereby in the storage unit 12.

The process carried out in this step Sa4 can also be performed in the computation unit 11 under the control of the host computer 16.

In step Sa5, the host computer 16 sets a variable $b_n$ to an initial value $b_{ini}$. The initial value $b_{ini}$ may be set arbitrarily as either one of value $b_1$ to value $b_m$. However, typically, it is set as either one of value $b_1$, value $b_m$, or an intermediate value among value $b_1$ to value $b_m$.

In step Sa6, the host computer 16 has the display 13 display a calculated image of b-factor=$b_n$ among which are generated in step Sa4.

In this manner, in a state where the calculated image is displayed in the display 13, the host computer 16 waits for a request to change the variable $b_n$ to be made in step Sa7. The request for changing the variable $b_n$ can be received, for example, by inputting the user operation of a slide bar displayed in the display 13 by the input device 14.

When the request for changing the variable $b_n$ is made, the host computer 16 proceeds from step Sa7 to step Sa8. In step Sa8, the host computer 16 changes the variable $b_n$ in accordance with the above request. Subsequently, the host computer 16 returns to step Sa6 and renews the display of the display 13 so that the calculated image of a b-factor corresponding to the variable $b_n$ after the change is displayed.

Figure 3:
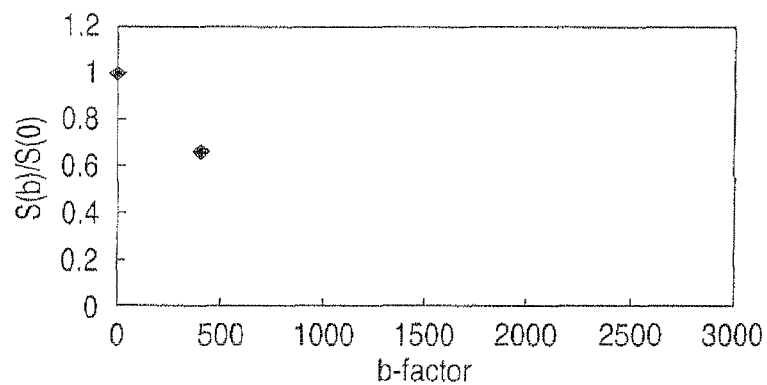
FIG. 3 shows an example of a relationship between two signal values regarding a same pixel, by imaging two actual original images.
Figure 4:
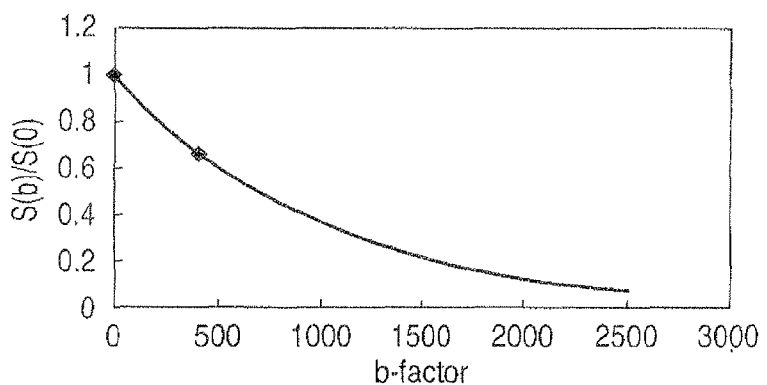
FIG. 4 shows an example of a function that is identified by an ADC obtained based on the two signal values shown in FIG. 3.
Figure 5:
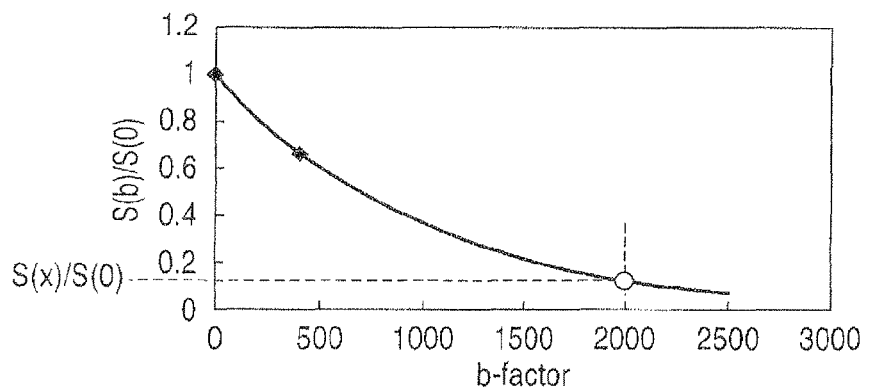
FIG. 5 shows an example of an aspect of obtaining a signal value regarding an arbitrary b-factor based on the function shown in FIG. 4.

In this manner, according to the first embodiment, an ADC that specifies a function as indicated by the curved line in FIG. 4 is derived for each pixel within the region of interest, based on the two signal values obtained by actual imaging as shown in, for example, FIG. 3. Based on this ABC, it is possible to estimate a signal value S(x) in an arbitrary b-factor as show in, for example, FIG. 5. A calculated image of the arbitrary b-factor can be obtained as an arrangement of pixels of signal values estimated in such manner. Thus, it is possible to obtain a diffusion-weighted image using a b-factor that is larger than that corresponding to the maximum gradient magnetic field intensity and the time of application of the MPG pulse.

Further, with regard to portions with large movement such as abdominal portions, by imaging the original image using a small b-factor to suppress a motion artifact, an image of a large b-factor can also have a motion artifact suppressed small.

According to the first embodiment, each of the calculated images obtained by setting a b-factor in different values from value $b_1$ to value $b_m$ by certain increments is displayed selectively in accordance with a slide bar operation. Therefore, a user is able to easily observe the difference in image when changing the b-factor.

Second Embodiment

An operation in a second embodiment of the magnetic resonance diagnostic apparatus 100 will be explained.

Figure 6:
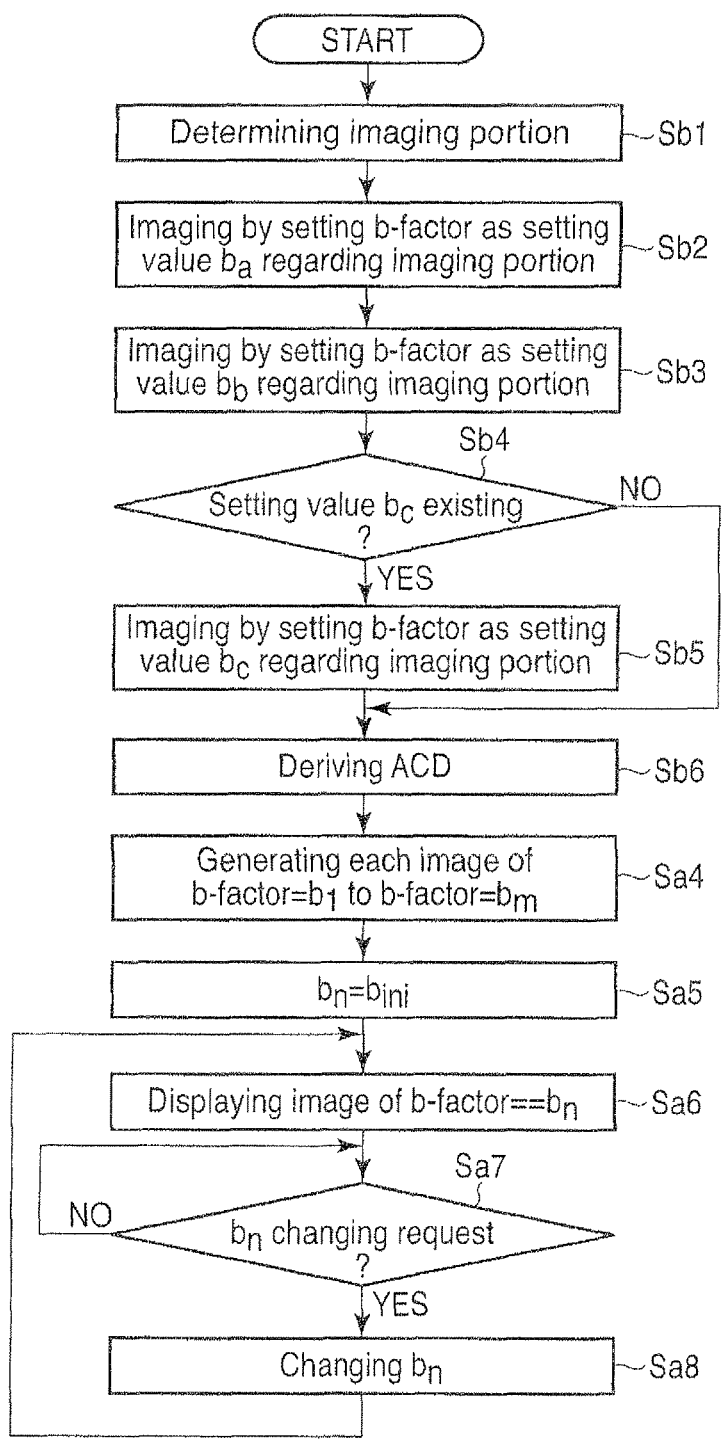
FIG. 6 is a flow chart showing a processing procedure in a second embodiment of a host computer illustrated in FIG. 1.

FIG. 6 shows a flow chart illustrating a process procedure in the second embodiment of the host computer 16. Further, the same symbols are given for processes that are the same as those in FIG. 2, and explanations thereof will be omitted.

In step Sb1, the host computer 16 determines the part of the subject to become the target for imaging in the subsequent processes (hereinafter referred to as an imaging portion). The imaging portion can be determined in accordance with the user's assignment input via, for example, the input device 14.

In step Sb2, the host computer 16 instructs the sequencer 10 to carry out imaging with regard to a preset region of interest, by setting the b-factor as a setting value $b_a$ regarding an imaging portion. In accordance with this instruction, the sequencer 10 operates the gradient power supply 7, the transmitter 9T, the receiver 9R and the computation unit 11 etc., so as to carry out imaging by using a b-factor that has value $b_a$. The image imaged here will be referred hereinafter as a first original image.

Meanwhile, in order to set the b-factor as the setting value $b_a$ that is related to the imaging portion, the storage unit 12 has, for example, an information table as shown in FIG. 7 stored in advance. In the information table shown in FIG. 7, there is written setting values $b_a$, $b_b$, $b_c$, and setting values $b_1$, $b_2$, $b_2$ in association with each of the plurality of portions of a human body. However, it is possible to set the setting value $b_c$ and setting values $b_2$, $b_2$ in a state of having no substantial values (null state). The setting values $b_a$, $b_b$, $b_c$, and setting values $b_1$, $b_2$, $b_2$ written in this information table are set with appropriate values based on a clinical standpoint. The information table is registered in the storage unit 12 at the stage of manufacturing the magnetic resonance diagnostic apparatus 100, or the ready-for-use stage of the magnetic resonance diagnostic apparatus 100.

In step Sb3, the host computer 16 operates the gradient power supply 7, the transmitter 9T, the receiver OR and the computation unit 11 etc., so as to carry out imaging by using a b-factor that has a value $b_b$. The image imaged here will be referred hereinafter as a second original image.

In step Sb4, the host computer 16 confirms whether or not the setting value $b_c$ is associated with an imaging portion in the information table. If there is a relevant setting value $b_c$, the host computer 16 proceeds from step Sb4 to step Sb5.

In step Sb5, the host computer 16 operates the gradient power supply 7, the transmitter 9T, the receiver 9R and the computation unit 11 etc., so as to carry out imaging by using a b-factor that has a value $b_c$. The image imaged here will be referred hereinafter as a third original image.

After the imaging is completed in step Sb5, or when there is no corresponding setting value $b_c$ in step Sb4, the host computer proceeds to step Sb6. In step Sb6, the host computer 16 derives ADC respectively for each pixel within the region of interest. Further, in the case where imaging of the third original image is not carried out, the derivation of ADC here can be performed likewise in the first embodiment. In the case where imaging of the third original image is carried out, ADC is derived by a so-called curve approximation as explained below.

The image value $S(b_n)$ of an original image in which the b-factor is $b_n$ (n=a, b, c) is in an exponential relationship that is determined by S (0) and ADC. This can be expressed in the following equation (5).

$$S(b_n)=S(0)\cdot\exp[-b_n\cdot ADC] \quad (5)$$

Here, for example, by using a method of least squares approximation, S (0) and ADC can be obtained from $b_a$, $b_b$, $b_c$ and S ($b_a$), S ($b_b$), S ($b_c$). Specifically, S (0) and ADC are determined so that the square sum of an error between the actual S ($b_a$), S ($b_b$), S ($b_c$) and the value calculated by the equation (5) becomes minimum.

Alternatively, by taking the logarithm of equation (5), an equation (6) is obtained.

$$\ln(S(b_n))=\ln(S(0))-b_n\cdot ADC \quad (6)$$

By taking $b_n$ as a horizontal axis and $\ln(S(b_n))$ as a vertical axis, this equation (6) takes $\ln(S(0))$ as an intercept of the vertical axis and becomes a straight line having an inclination of $-ADC$. Therefore, it is fine to determine $\ln(S(0))$ and ADC that best place the three points on this straight line by a least-square method.

Subsequently, the host computer 16 carries out the processes of step Sa4 to step Sa8 in the same manner as the first embodiment. However, for values $b_1$ to $b_m$, values specified in the above mentioned information table will be employed.

By the way, it is possible to derive ADC by using any b-factor to obtain an original image. However, since the degree of impact of the MPG differs depending on the portion of the human body, the accuracy of the derived ADC changes depending on the b-factor applied to obtain the original image. Therefore, in the second embodiment, the b-factor to be applied to obtain the original image is changed in accordance with the imaging portion. By doing so, in the case of imaging any portion of the subject, ADC can be derived with good accuracy to generate a further adequate calculated image.

Further, in the second embodiment, ADC can be derived based on three original images. In this case, ADC can be derived with higher accuracy than based on two original images, and a further adequate calculated image can be generated.

Further, in the second embodiment, the b-factor to be applied for generating the calculated image is also changed in accordance with the imaging portion. Therefore, the calculated image can be generated the same as when imaging using a b-factor that is suitable for observing the imaging portion.

Furthermore, a same portion may have different degree of MPG impact depending on the symptoms (such as the existence or non-existence of abnormality, or the degree of abnormality) of the portion. Therefore, it is also fine to specify in the information table each setting value in association with the combination of the imaging portion and the symptoms.

Third Embodiment

The operation in a third embodiment of the magnetic resonance diagnostic apparatus 100 will be explained.

Figure 8:
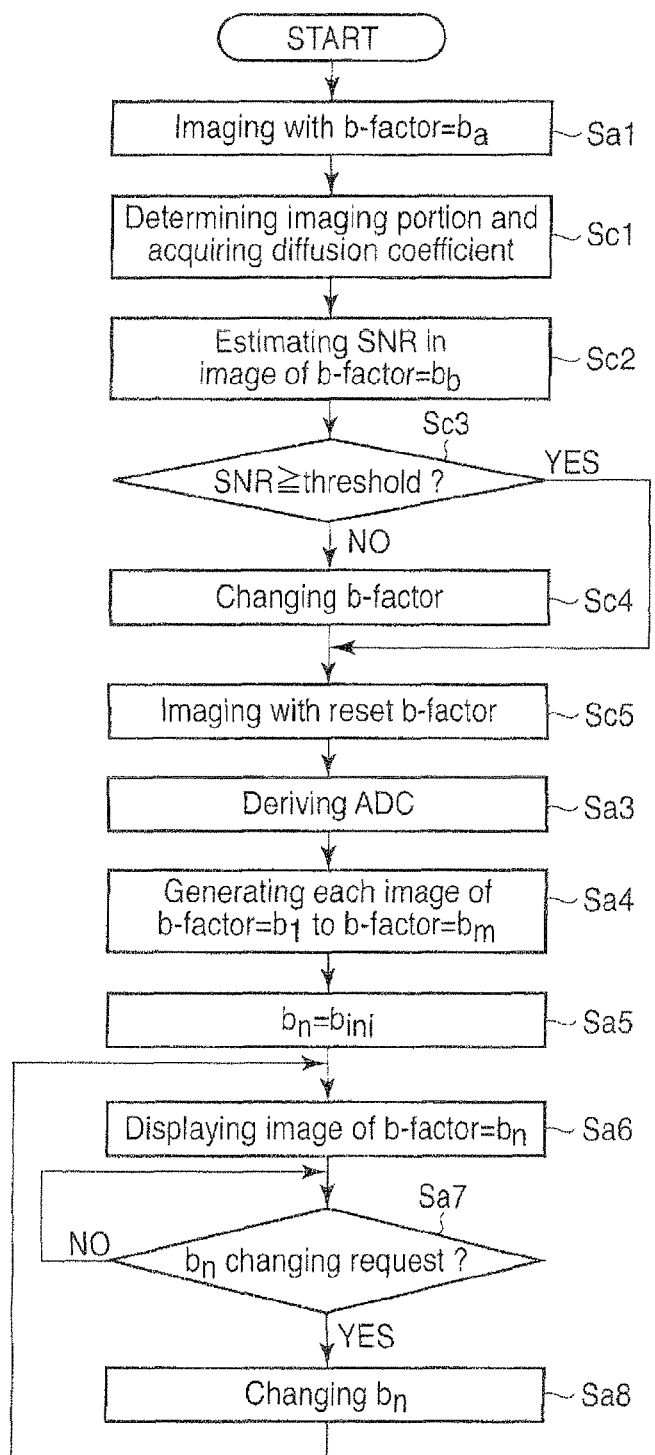
FIG. 8 is a flow chart showing a processing procedure in a third embodiment of a host computer illustrated in FIG. 1.

FIG. 8 is a flow chart showing the process procedure in the third embodiment of the host computer 16. Further, the same symbols are given for processes that are the same as in FIG. 2, and explanations thereof will be omitted.

Firstly, in step Sa1, the host computer 16 images the first original image in the same manner as in the first embodiment, then proceeds to step Sc1.

In step Sc1, the host computer 16 determines the imaging portion and acquires a diffusion coefficient D regarding the imaging portion thereof. A diffusion coefficient differs for each anatomy in the human body. Further, a standard diffusion coefficient in a normal tissue is already known. Therefore, an information table as shown in FIG. 9 that specifies the standard diffusion coefficient of an anatomy that may become the imaging portion is stored in the storage unit 12 in advance in association with each of the anatomy thereof. In step Sc1, the host computer 16 acquires the value associated with the imaging portion in the information table as the diffusion coefficient D.

In step Sc2, the host computer 16 estimates the SNR in the second original image that is obtained by carrying out imaging regarding the above mentioned region of interest, by setting the b-factor as value $b_b$, which is predetermined to be different from value $b_a$. Specifically, firstly, the host computer 16 is able to estimate the signal value $S(b)$ of the second original image by the following equation, which expresses the signal value in the first original image as $S(a)$. Meanwhile, since a noise level undergoes small changes by the impact of MPG, the noise levels between the first original image and the second original image are almost the same. Therefore, the SNR in the second original image can be estimated by the ratio between the signal value $S(b)$ that is obtained by the following equation and the noise level in the second original image.

$$S(b) = S(a) \cdot \exp(-b_b \cdot D)$$

As can be understood from the above equation, since the signal value $S(b)$ decreases when the b-factor increases, SNR also decreases.

In step Sc3, the host computer 16 confirms whether or not the SNR estimated as above is equal to or exceeds the predetermined threshold value. If the SNR is lower than the threshold value, the host computer 16 proceeds from step Sc3 to step Sc4.

In step Sc4, the host computer changes the b-factor so that the SNR becomes equal to or exceeds the threshold value.

In the case where the process of step Sc4 is completed, or in the case where SNR is judged as being equal to or exceeding the threshold value in step Sc3, the host computer 16 proceeds to step Sc5.

In step Sc5, the host computer 16 acquires the second image by carrying out imaging regarding the above mentioned region of interest with the b-factor that is changed in the case of performing step Sc4, and with the b-factor set as value $b_b$ in the case where step Sc4 has been skipped.

Subsequently, the host computer 16 performs the processing of steps Sa3 to Sa8 in the same manner carried out in the first embodiment.

In the case of utilizing an original image with low SNR, contribution of noise increases, and the accuracy of the derived ADC deteriorates. Further, therefore, the error between the calculated image generated based on ADC including a lot of errors and the image actually taken increases. However, in the third embodiment, since an original image with sufficiently large SNR is used to derive ADC, the ADC can be derived with high accuracy. In this manner, according to the third embodiment, a calculated image that is close to the actually imaged image can be generated.

This embodiment can carry out various modified implementations as follows.

Unnecessary regions such as air portions within the region of interest may be judged based on the original image, to calculate the ADC regarding only the pixel in a region where the unnecessary regions have been removed, or to estimate a signal value of an arbitrary b-factor.

Only the calculated image of a b-factor assigned by a user may be generated and displayed.

The generated calculated image may be output to another apparatus to have it displayed on a displayer of the apparatus.

An image imaged by another apparatus can be used as the original image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance diagnostic apparatus comprising:
MRI gantry components comprising static and gradient magnetic field generators, at least one radio frequency (RF) coil coupled to an imaging volume, transmitter and receiver and computer circuits connected to control said gradient magnetic field generator, said transmitter and said receiver, said computer circuits being configured to:
obtain at least two original MR images by imaging, using said MRI gantry components, an imaging region on a subject using at least two b-factors, respectively;
derive an apparent diffusion coefficient regarding a pixel position for each pixel position included in a region of interest in the at least two original images, based on pixel values of each of the at least two original images regarding the pixel positions; and
estimate a pixel value obtained by using a b-factor which is different from the at least two b-factors, regarding each pixel position included in the region of interest, based on the apparent diffusion coefficient derived for each pixel position; and
generate a calculated image by arranging the estimated pixel values with respect to each of the pixel positions;
wherein the at least two b-factors are set in accordance with a portion of the subject included in the imaging region.

2. The magnetic resonance diagnostic apparatus according to claim 1, wherein the at least two b-factors are set for each of a plurality of portions of the subject, and further comprising data store configured to store the at least two b-factors set for the portion, in association with each of the plurality of portions, wherein the at least two original images are obtained by using the at least two b-factors, respectively, which are stored in association with the portion of the subject included in the imaging region.

3. The magnetic resonance diagnostic apparatus according to claim 2, wherein the at least two b-factors are set for each of plural combinations of symptoms regarding the plurality of portions and the portion.

4. The magnetic resonance diagnostic apparatus according to claim 1, wherein the a pixel value is estimated using a b factor which is larger than the at least two b-factors.

5. The magnetic resonance diagnostic apparatus according to claim 1, wherein the apparent diffusion coefficient is derived for only pixels in a region excluding a region of the at least two original images outside said region of interest.

6. The magnetic resonance diagnostic apparatus according to claim 1, further comprising a user input interface wherein a b-factor is set which is different from the at least two b-factors as a value assigned by a user.

7. The magnetic resonance diagnostic apparatus according to claim 6, further comprising:
a display configured to display the calculated image, and wherein when a user causes a b-factor to be changed, the calculated image display is changed accordingly.

* * * * *